United States Patent
Shi et al.

(10) Patent No.: US 9,863,761 B2
(45) Date of Patent: Jan. 9, 2018

(54) CRITICAL DIMENSION UNIFORMITY MONITORING FOR EXTREME ULTRAVIOLET RETICLES

(71) Applicant: KLA-Tencor Corporation

(72) Inventors: Rui-fang Shi, Cupertino, CA (US); Alex Pokrovskiy, San Jose, CA (US); Abdurrahman Sezginer, Monte Serano, CA (US); Weston L. Sousa, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 324 days.

(21) Appl. No.: 14/390,834

(22) PCT Filed: Apr. 16, 2013

(86) PCT No.: PCT/US2013/036702
§ 371 (c)(1),
(2) Date: Oct. 6, 2014

(87) PCT Pub. No.: WO2013/158593
PCT Pub. Date: Oct. 24, 2013

(65) Prior Publication Data
US 2015/0144798 A1    May 28, 2015

Related U.S. Application Data

(60) Provisional application No. 61/635,141, filed on Apr. 18, 2012.

(51) Int. Cl.
*G01B 11/24* (2006.01)
*G03F 1/22* (2012.01)
(Continued)

(52) U.S. Cl.
CPC ............ *G01B 11/24* (2013.01); *G01B 11/02* (2013.01); *G01N 21/8806* (2013.01); *G03F 1/22* (2013.01);
(Continued)

(58) Field of Classification Search
CPC ......... G03F 7/705; G03F 1/70; G06T 7/0006; G06T 7/001; G01N 2021/95615; G06F 17/5081
See application file for complete search history.

(56) References Cited

U.S. PATENT DOCUMENTS 6,590,219 B1 * 7/2003 Ziger .................. G03F 7/70191
                                                        250/492.2
7,488,933 B2 * 2/2009 Ye ........................... G03F 7/705
                                                        250/252.1
(Continued)

FOREIGN PATENT DOCUMENTS

CN        1845009 A    10/2006
CN     101042527 A     9/2007
(Continued)

OTHER PUBLICATIONS

"International Application No. PCT/US2013/036702, International Search Report and Written Opinion dated Jul. 30, 2013", 6 pgs.
(Continued)

*Primary Examiner* — Kenneth J Malkowski
(74) *Attorney, Agent, or Firm* — Kwan & Olynick LLP

(57) ABSTRACT

Disclosed are methods and apparatus for facilitating an inspection of a sample using an inspection tool. An inspection tool is used to obtain an image or signal from an EUV reticle that specifies an intensity variation across the EUV reticle, and this intensity variation is converted to a CD variation that removes a flare correction CD variation so as to generate a critical dimension uniformity (CDU) map
(Continued)

without the flare correction CD variation. This removed flare correction CD variation originates from design data for fabricating the EUV reticle, and such flare correction CD variation is generally designed to compensate for flare differences that are present across a field of view (FOV) of a photolithography tool during a photolithography process. The CDU map is stored in one or more memory devices and/or displayed on a display device, for example, of the inspection tool or a photolithography system.

18 Claims, 7 Drawing Sheets

(51) Int. Cl.
*G03F 1/70* (2012.01)
*G01B 11/02* (2006.01)
*G01N 21/88* (2006.01)

(52) U.S. Cl.
CPC ............ *G03F 1/70* (2013.01); *G01B 2210/56* (2013.01); *G01N 2201/06113* (2013.01)

(56) References Cited

U.S. PATENT DOCUMENTS

| | | |
|---|---|---|
| 2006/0240336 A1 | 10/2006 | Watson et al. |
| 2008/0180649 A1 | 7/2008 | Hansen |
| 2009/0053628 A1 | 2/2009 | Ye et al. |
| 2010/0208978 A1* | 8/2010 | Terasawa ............... B82Y 10/00 382/145 |
| 2011/0161893 A1 | 6/2011 | Lin et al. |

FOREIGN PATENT DOCUMENTS

| | | |
|---|---|---|
| CN | 102193302 A | 9/2011 |
| CN | 102200692 A | 9/2011 |
| KR | 20090037188 A | 4/2009 |
| KR | 1020090044565 | 5/2009 |
| TW | 200746343 A | 12/2007 |
| TW | 200941611 A | 10/2009 |
| WO | 2009115329 A1 | 9/2009 |
| WO | 2013158593 A1 | 10/2013 |

OTHER PUBLICATIONS

Scaccabarozzi, Luigi et al., "Cleaning and Inspection of EUV Reticles: Specifications and Prospects", ASML Netherlands, Technical University Eindhoven, Retrieved from the Internet: http://www.mstconf.com/UMaine%20Presentations/Particle11ManuScaccabarozzi.pdf, Accessed on Apr. 2, 2013, 23 pgs.
"Int'l Application Serial No. PCT/US2013/036702, Preliminary Report on Patentability dated Oct. 30, 2014", 10 pgs.
"Chinese Application Serial No. 201380030349.3, Office Action dated Jun. 1, 2016", 11 pgs.
Seo, Kangjoon et al., "New Critical Dimension Uniformity Measurement Concept Based on Reticle Inspection Tool", Proc. of SPIE, vol. 7748, 2010, 8 pgs. Retrieved from the Internet: http://proceedings.spiedigitallibrary.org/ConferenceProceedings.aspx, Accessed on Aug. 26, 2016.
"171860 TW Office Action with Search Report", 43 pages.

* cited by examiner

CRITICAL DIMENSION UNIFORMITY MONITORING FOR EXTREME ULTRAVIOLET RETICLES

CROSS-REFERENCE TO RELATED APPLICATION

This application is a U.S. national application under 5 U.S.C. 371 of PCT Application No. PCT/US13/36702, entitled CRITICAL DIMENSION UNIFORMITY MONITORING FOR EXTREME ULTRA-VIOLET RETICLES, filed 16 Apr. 2013 by Rui-fang Shi et al., which claims priority of U.S. Provisional Patent Application No. 61/635,141, entitled CRITICAL DIMENSION UNIFORMITY MONITORING FOR EUV RETICLES, filed 18 Apr. 2012 by Rui-Fang Shi et al. These applications are incorporated herein by reference in their entirety for all purposes.

TECHNICAL FIELD OF THE INVENTION

The invention generally relates to the field of reticle inspection and metrology. More particularly the present invention relates to inspection and measurement of extreme ultra-violet (EUV) reticle for monitoring critical dimension (CD) uniformity.

BACKGROUND

Generally, the industry of semiconductor manufacturing involves highly complex techniques for fabricating integrating circuits using semiconductor materials which are layered and patterned onto a substrate, such as silicon. An integrated circuit is typically fabricated from a plurality of reticles. Initially, circuit designers provide circuit pattern data, which describes a particular integrated circuit (IC) design, to a reticle production system, which transforms the pattern data into a plurality of reticles. One emerging type of reticle is an extreme ultraviolet (EUV) reticle that is comprised of a plurality of mostly reflecting layers and a patterned absorber layer.

Due to the large scale of circuit integration and the decreasing size of semiconductor devices, the reticles and fabricated devices have become increasingly sensitive to critical dimension (CD) uniformity variations. These variations, if uncorrected, can cause the final device to fail to meet the desired performance due to electrical timing errors. Even worse, they can cause final device to malfunction and adversely affect yield.

It would be beneficial to provide techniques that are suitable for inspecting and measuring EUV reticles to monitor CD uniformity.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of facilitating an inspection of a sample using an inspection tool is disclosed. An inspection tool, such as a deep ultraviolet (DUV) tool, is used to obtain an test image or signal from an EUV reticle that specifies an intensity variation across the EUV reticle, and this intensity variation is converted to a CD variation that removes a correction CD variation (e.g., for flare or azimuthal angle compensation in the lithographic tool) so as to generate a critical dimension uniformity (CDU) map without the correction CD variation. This removed correction CD variation originates from design data for fabricating the EUV reticle, and such correction CD variation is generally designed to compensate for differences (e.g., flare) that are present across a field of view (FOV) of a photolithography tool during a photolithography process. The CDU map is stored in one or more memory devices and/or displayed on a display device, for example, of the inspection tool or a photolithography system. In a specific embodiment, the CDU map is generated with respect to the designer's intent prior to introduction of flare correction or azimuthal angle CD variation to the design data for such EUV test reticle so as to compensate for flare or azimuthal angle differences across the FOV. In a further example, the CDU map is generated so as to account for vertical or horizontal feature bias.

In a specific implementation, the CDU map is generated by (i) determining a conversion factor for converting between intensity variation and CD variation based on the design data for the EUV test reticle, (ii) converting the intensity variation of the test image into a CD variation for such test image, (iii) based on the design data, determining the correction CD variation, and (iv) subtracting the correction CD variation from the CD variation for the test image to generate the CDU map. In a further aspect, the conversion factor is determined by performing rigorous electromagnetic simulations by applying a model on the design data so as to model construction of a reticle model from such design data and so as to model inspection of such reticle model to generate a reference image that substantially matches the test image. In yet a further aspect, performing rigorous electromagnetic simulations on the design data comprises selecting different sets of tunable parameter values of the model and applying such model to generate the reference image until the reference image substantially matches the test image, wherein the tunable parameter values comprise one or more of the following: pattern CD, reticle fabrication variables, reticle material properties, and inspection tool parameters. In one aspect, the conversion factor takes the form of a table of associated intensity and CD variation values. In another aspect, the correction CD variation is determined by determining a CD difference between pre-correction design data and post-correction design data.

In another embodiment, the CDU map is generated by (i) pre-computing a conversion factor for converting between intensity variation and CD variation based on the design data for a sample reticle and a sample image obtained from such sample reticle, (ii) using the pre-computed conversion factor, converting the intensity variation of the test image of the EUV test reticle into a CD variation for such test image so as to generate a first CDU map, (iii) fitting the first CDU map to a flare correction CD variation map, and (iv) subtracting the flare correction CD variation map from the first CDU map for the test image to generate a second CDU map.

In a further aspect, the CDU map is generated without the EUV test reticle's design data. In another aspect, the operations for converting, fitting, and subtracting are repeated for a plurality of subsequent EUV test reticles based on the pre-computed conversion factor without computing another conversion factor for such subsequent EUV test reticles. In one aspect, the fitting operation is performed by minimizing a summation equal to $\Sigma_{x,y}[\Delta CD(x,y)/CD(x,y) - f(\text{coeff}, F(x,y))]^2$, where the summation is taken over the points of the first CDU map, which is represented by ΔCD(x,y)/CD(x,y) and f(coeff, F(x,y)) is a polynomial of F, and wherein F(x,y) is a map of flare intensity that is estimated by calculating a pattern density map and convolving such pattern density map with a point-spread function, and wherein f(coeff, F(x,y)) is the estimate of a CD compensation for the flare intensity In another embodiment, the CDU map is generated by (i) based on the design data for the EUV test reticle, identifying selected features for CD measurement, (ii) measuring CD for the selected features by measuring a distance between isofocal threshold intensity points for the selected features in the test image or by minimizing a difference between a simulated reference image generated from the design data and the test image while floating a single parameter that characterizes CD bias, (iii) determining CD variation based on the measured CD, (iv) based on the design data, determining the correction CD variation, and (v) subtracting the correction CD variation from the CD variation for the test image to generate the CDU map.

In other embodiments, the invention pertains to an inspection system for inspecting an EUV reticle. The system includes a light source for generating an incident beam, an illumination optics module for directing the incident beam onto an EUV reticle, a collection optics module for directing an output beam that is reflected from the EUV reticle in response to the incident beam, a sensor for detecting the output beam and generating an image or signal for the output beam, and a controller that is configured to perform one or more of the above methods.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

Figure 1:
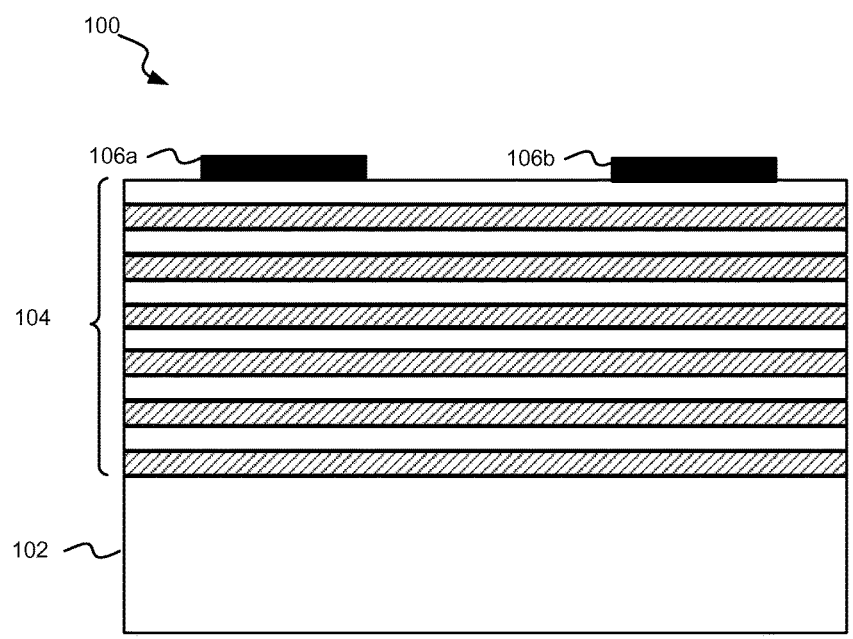
FIG. 1 is a diagrammatic representation of a side view of an example EUV reticle.

An extreme ultraviolet (EUV) lithography process typically uses an EUV type reticle that is designed to facilitate patterning on a wafer at EUV wavelengths, such as 13.5 nm. FIG. 1 is a diagrammatic representation of a side view of a portion of an example EUV reticle. As shown, the EUV reticle 100 may include a substrate 102, such a low thermal expansion (LTE) or ultra-low expansion (ULE) glass plate.

The substrate is covered with multiple layers 104 of materials to provide moderate reflectance (e.g., 60-70% or more) at the EUV wavelength for performing lithographic exposure at EUV wavelengths. The multilayer stack 104 serves as a Bragg reflector that maximizes the reflection of EUV radiation while being a poor absorber of the EUV radiation. Reflection generally occurs at interfaces between materials of different indices of refraction with higher differences causing more reflectivity. Although indices of refraction for materials exposed to wavelengths that are extremely low are about equal to 1, significant reflection can be achieved through use of multiple layers having alternating layers of different refractive indices. The multilayer stack also may be comprised of low absorption characteristics so that the impinging radiation is reflected with little loss. In certain embodiments, the multiple layers 104 include between about 30 to 40 (or 40 to 50) alternating pairs of molybdenum (Mo) and silicon (Si) layers arranged with about 7 nanometer pitch. Other suitable layers may include alternating layers of $Mo_2C$ and Si, Mo and beryllium (Be), molybdenum ruthenium (MoRu) and Be.

The multiple layers 104 may include a capping layer, such as Ru, to prevent oxidation. In other embodiments, an EUV reticle may include a quartz, antireflective coating (ARC), and other features. A pattern (e.g., 106a and 106b) is formed in an absorber layer that is disposed over the multiple layers 104. For example, a tantalum boron nitride film topped by a thin anti-reflective oxide acts as an EUV absorber. The material(s) used for the reticle pattern may be selected to have nearly zero etch bias so as to achieve ultra-fine resolution features.

Figure 2:
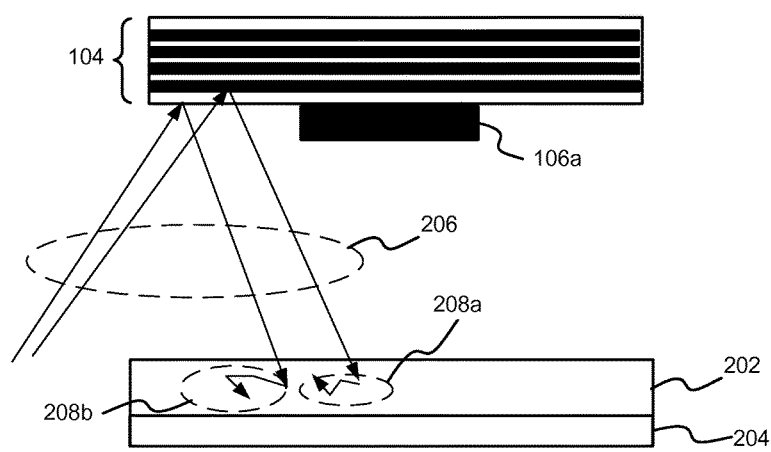
FIG. 2 illustrates a side view perspective of an EUV reticle and wafer in an EUV photolithography process.

In general, any suitable EUV photolithography process may be implemented to expose a photoresist layer on a wafer via an EUV reticle. FIG. 2 illustrates a side view perspective of a reticle and a wafer sample in an EUV photolithography process. The light source of a photolithography system may produce any suitable radiation that is suitable for use with EUV reticles. For instance, EUV wavelengths between about 11 to 14 nm or lower soft x-ray wavelengths may be utilized. In a specific implementation, a wavelength of about 13.5 nm is produced.

During photolithography, radiation 206 that is reflected from the multiple layers 104 of an EUV reticle is absorbed in a resist layer 202 formed on a wafer substrate 204. The absorbed radiation produces photoacids (H+) and amplified photoacids (e.g., 208a and 208b) that form an exposed pattern in the resist layer 202 of the wafer substrate 204 that corresponds to the absorber pattern layer, e.g., 106a, of the EUV reticle when the photo resist is developed. Reflective imaging optics between the EUV reticle and the wafer is omitted in FIG. 2 for clarity.

Prior to use of EUV lithography, optical reticle patterns were designed to have identical die patterns that produce identical dies on a wafer. In contrast, EUV reticles are designed to have different die patterns to produce identical dies on a wafer. One of the reasons for this is that the field of the lithography projector has an arc-shape. The wafer and the reticle are synchronously scanned through the field, in a direction that is perpendicular to the arc. The azimuthal angle of the chief ray on the mask varies along the arc-shaped field. Different types of features, such as horizontal vs. vertical features with respect to the beam scan, cause a different shadow effect. This difference varies along the arc. Therefore, dies aligned in the scan direction are more similar than dies on different field locations. A second reason for dies having different patterns on the reticle is that the edge of a die that is also at the edge of the exposure field can differ from the edge of a die that is internal to the exposure field. The lithography projector steps the wafer and repeats the scan in an unexposed portion of the wafer. The edges of neighboring exposure fields overlap. The overlapping edge is exposed twice and corners can be exposed four times. No circuit pattern is multiply exposed, and measures may be taken to reduce the reflection of the reticle at the edge of the exposure field. Nevertheless, the double exposure can cause a subtle difference in the flare exposure at the edge of the exposure field. A third possible reason for differences between die patterns on the reticle is that different portions of the light with respect to the lithography tool's field of view (FOV) will exhibit different scattering properties. For instance, light from different optical paths (e.g., different angles and different surface smoothness characteristics) will scatter differently across the FOV. The reticle patterns need to be designed to compensate for this different scattering effect, commonly referred to as a flare effect. Different FOV positions of the reticle may be designed differently to compensate for different flare levels and different azimuth angle of the chief ray.

Since the reticle will tend to contain different die patterns for different FOV locations for flare correction, it may be difficult to characterize critical dimension uniformity (CDU) or measure actual critical dimension (CD) across the reticle. That is, the CD characteristics for a reticle may be skewed by the CD differences that were designed into the reticle pattern to compensate for flare and azimuthal angle dependence of the chief ray.

Certain embodiments of the present invention provide techniques for determining CD characteristics based on intensity results obtained from an optical inspection tool while filtering compensation CD characteristics (e.g., flare or other types of CD corrective variation) from such determined CD characteristics. In general, CD variations or measurements across the EUV reticle are obtained, and these results are obtained with respect to the designer's intent prior to compensation of the design for field-position-dependent effects such as flare and chief-ray azimuth angle variation. In other words, the compensation CD characteristics are treated as a noise source and removed so that the compensation CD characteristics do not overshadow the CD characteristics of the reticle that would be present if flare or chief-ray azimuth angle variation and their compensation were absent. In specific implementations, inspection results or CD characteristics are determined in a way so as to account for vertical/horizontal feature bias.

Figure 3:
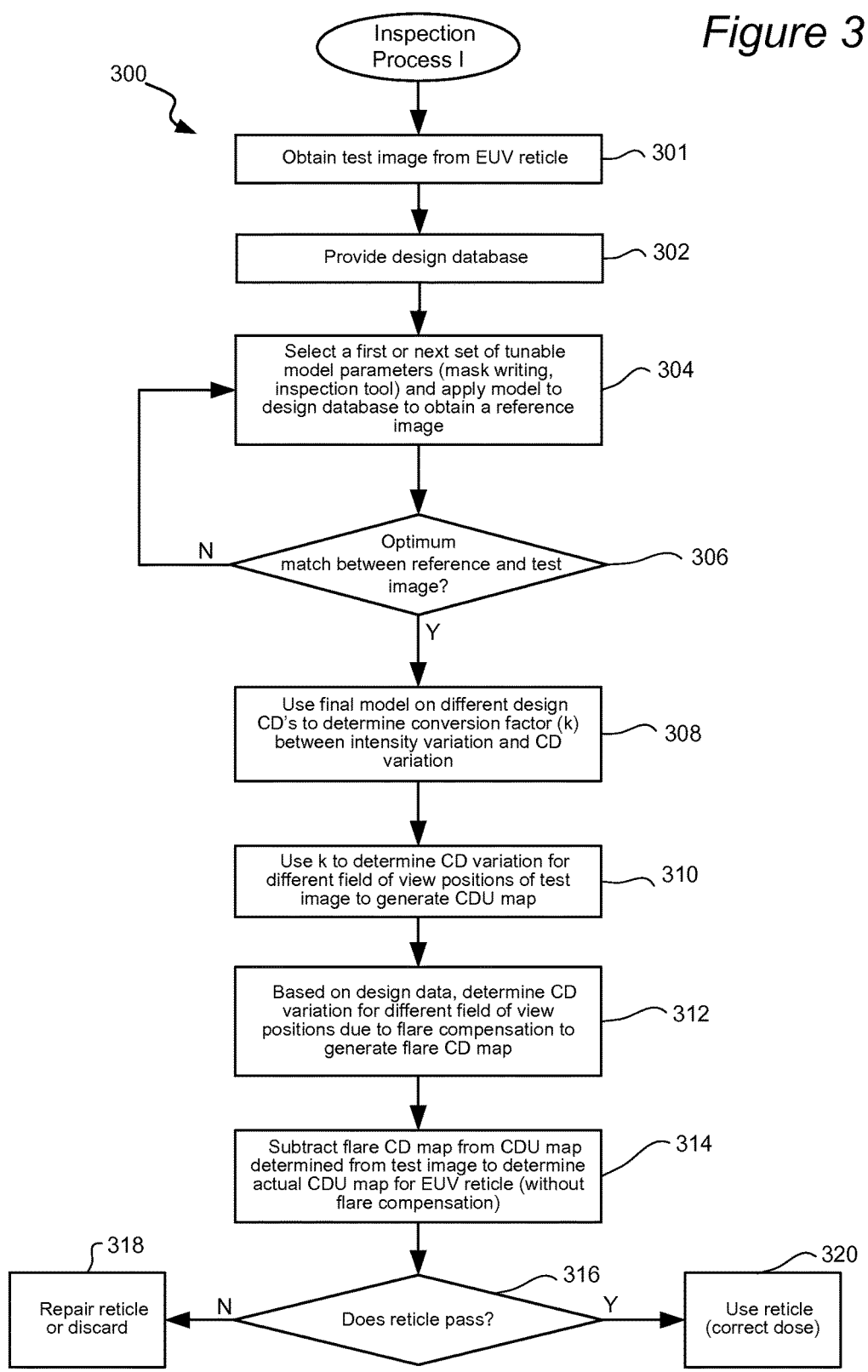
FIG. 3 is a flow chart illustrating a procedure for inspecting an EUV reticle in accordance with a first implementation of the present invention.

In a first inspection and measurement approach, a design database is used to account for flare compensation and vertical/horizontal bias. FIG. 3 is a flow chart illustrating a procedure 300 for inspecting an EUV reticle in accordance with a first implementation of the present invention. The inspection procedure 300 may be performed on the reticle after fabrication of such reticle and prior to such reticle being used in a photolithography process and again at any time after the reticle has been used in one or more photolithography processes. Additionally, the following operations may be applied with respect to any one or more portions of a reticle. For instance, the reticle image may be defined as a plurality of patch images that are processed by a plurality of processors. The reticle patches may be distributed to processors that operate on the test patch data in parallel. Although not required, the operations of FIG. 3 can be performed in parallel for multiple patches of a reticle image.

Initially, a test image of an EUV reticle may be obtained in operation 301. In one embodiment, patch portions of the reticle can be scanned to obtain intensity data from the entire reticle. Each patch may contain a single die or multiple dies. A patch may have any size and shape, depending on the particular system and application requirements. In general, multiple intensity values for each patch portion may be obtained by scanning the reticle in any suitable manner. By way of example, multiple intensity values for each patch may be obtained by raster scanning the reticle. Alternatively, the images may be obtained by scanning the reticle with any suitable pattern, such as a circular or spiral pattern. Of course, the sensors (one or more) may have to be arranged differently (e.g., in a circular pattern) and/or the reticle may be moved differently (e.g., rotated) during scanning in order to scan a circular or spiral shape from the reticle.

In one example, as the reticle moves past sensors of an inspection/metrology tool, light is detected from a rectangular region (herein referred to as a "swath") of the reticle and such detected light is converted into multiple intensity values at multiple points in each patch of the swath. In this embodiment, the sensors of the inspection/metrology tool are arranged in a rectangular pattern to receive light that is reflected from the reticle and generate therefrom intensity data that corresponds to a swath of patches of the reticle. In a specific example, each swath can be about 1 million pixels wide and about 1000 to 2000 pixels high, while each patch can be about 1000 pixels wide and 1000 to 2000 pixels high. In one example, each pixel has a size of 72 nm.

Each set of intensity data may correspond to a "swath" of the reticle. Each set of intensity data may be obtained by sequentially scanning swaths from the reticle in a serpentine or raster pattern. For example, a first swath of the reticle 600 is scanned by an optical beam of an optical inspection system from left to right to obtain a first set of intensity data. A second swath is then scanned from right to left to obtain a second set of intensity data. Each set of swath data may also be divided into patches. During or after intensity data is collected for multiple points in each patch of each swath, an average intensity value may also be determined for any portions of each patch or set of one or more patches, for example, of each test image.

Intensity values for each patch may be obtained using an optical inspection tool that is set up in any suitable manner. For an EUV reticle, an optical inspection tool is generally set up with a set of operating parameters or a "recipe" for obtaining reflected intensity values. Recipe settings may include one or more of the following settings: a setting for scanning the reticle in a particular pattern, pixel size, setting for grouping adjacent signals from single signals, focus setting, illumination or detection aperture settings, incident beam angle and wavelength settings, other detector settings, a setting for the amount of reflected light, etc.

A design database may be provided in operation 302. The design database may be used to determine a conversion factor k for converting between intensity variation in an optical image and CD variation. The conversion factor may be determined by performing rigorous electromagnetic simulations on the design data so as to model the construction of a reticle model from such design data and model optical inspection of such reticle model to generate a reference image. For instance, the model simulates a reticle pattern by simulating a process for altering the design data patterns in a same way as such design patterns are altered to form the actual test reticle, e.g., corners of the design polygons are rounded, etc. The model also simulates a reference image that is generated from such simulated reticle pattern by modeling the particular inspection tool to generate a test image from the actual test reticle. More specifically, the model simulates how light is reflected from the simulated reticle and detected by the inspection tool's optics and sensor and simulates a reference image based on such detected light. Example modeling software for reticle fabrication simulation and inspection tool simulation are PRO-LITH™ available from KLA-Tencor of Milpitas, Calif.

A first set of tunable model parameters for simulating a reference image based on the design data may first be selected in operation 304. This model is also applied to the design data to generate a simulated reference reticle image in operation 304. Since defects typically represent a small percentage of the pixels in a reticle image, a majority of the modeled reference reticle image's pixels, except for defects, will match the test image when the tunable model parameters have been optimized. That is, when the model most closely simulates how the actual test reticle was made and how a test image is obtained from such test reticle by the chosen inspection tool, the simulated reference image will also tend to closely match the test image. Thus, once the particular reticle process that was used to make the test reticle and the inspection tool that was used to generate the test image is understood and correctly modeled, an accurate reference image that most closely matches the test image (and how it was formed) can be simulated.

The tunable parameters of the model may take any suitable form for generating a corresponding reticle image. The tunable parameters may pertain to reticle writing characteristics, such as corner rounding amount, reticle material properties (e.g., composition and dimensions), pattern density dependent bias, etc., for constructing a reference reticle from the design data and inspection tool characteristics, such as illumination and detection aperture settings, polarization, focus, aberration characteristics, wavelength, pixel size, incident angle, etc., for modeling the same optical inspection tool that is being used to generate the test image from the test reticle. The inspection tool model is applied to the modeled reference reticle pattern to construct a reference image based on the design data. The modeled reference image corresponds to how a reticle that is constructed with the design data without any defects is imaged onto the inspection tool's sensor.

After the model is applied to the design data using each set of selected tunable parameters, it may then be determined whether an optimum match between the generated reference image and the corresponding test image has been reached in operation 306. For instance, each particular test patch image is compared to its corresponding reference patch image that was generated from the design database portion. Each test image and corresponding reference image may comprise a plurality of pixels having varying intensity values. Alternatively, the test and reference reticle portions may be represented by a plurality of intensity values for the plurality of xy positions in the reticle portion.

The tunable parameters will result in an optimum match after a particular number of iterations are performed through selecting different combinations of tuning parameter values. For instance, an optimum match may correspond to a set of parameters that result in a minimum difference between the test image and modeled reference image. An optimum match may be defined as the condition when a norm of difference of two images cannot be substantially reduced by changing adjustable parameters of the match. A suitable norm is the square root of the sum of squares of pixel by pixel differences of the two images or sum of squares of the differences.

In the illustrated embodiment, if the optimum match between the particular reference and test image has not been found, a next set of tunable parameters are selected for the model, which is applied to the design data to produce a new reference image in operation 304. A next set of parameter values are repeatedly selected in operation 304 until an optimum match between the reference and test image has been found.

Once an optimum match is found, the intensity differences between the test image and the reference image may also be flagged and stored as defects. These defects may also be analyzed to determine whether such defects are within specifications. For example, the defects can be analyzed to determine whether such defects represent real, fault defects or noise.

The final model, which resulted in the optimum match, may then be used to determine a conversion factor k for converting between intensity variation and critical dimension uniformity (CDU) in operation 308. The conversion factor k can then be used to determine CD variation for different field of view (FOV) positions of the test image to generate a CDU map in operation 310. For instance, k is applied to the test image intensity values to determine intra-field CD variation across the reticle. In a specific implementation, CDU corresponds to a dominant or average CD value for a particular reticle portion with respect to a global average or dominant CD value. The global average or dominant CD value may be found with respect to the entire reticle or a portion of the reticle.

In a specific implementation, the relationship between $\Delta I/I$ and $\Delta CD/CD$ is denoted by the formula of $\Delta CD/CD = k$ (pitch, CD)$*\Delta I/I$, where I denotes the measured averaged intensity (e.g., within about a 100 um length scale) and $\Delta I$ denotes the variation from the globally averaged intensity. The variable k is the conversion factor that relates to the final model. That is, the conversion factor k depends on the final parameters of the final model. In the above equation for the conversion factor (k), its dependence on pitch (p) and CD is meant to illustrate the one-dimensional pattern case. For two-dimensional cases, p and CD can be replaced by an actual description of patterns in the form of polygons or trapezoids.

The conversion factor may be determined in any suitable manner. For example, the model can be applied to a first set of line features having a particular pitch and nominal CD, such as 100 nm. The model outputs a first average intensity value for such 100 nm features. The CD of such first set of line features is then altered (from nominal CD) and the model outputs the resulting change in intensity for such first set of features. That is, the simulated reticle pattern's CD can be altered and the final model is applied to such adjusted CD changes so as to output the corresponding modeled intensity changes in the modeled reticle image. The relationship (k) between changes in CD and changes in intensity may be determined by iterating through a plurality of CD changes in the reticle model. This process can be applied to any number and type of features. For arbitrary two-dimensional patterns, an isotropic expansion or shrinking of features sizes in all orientations can be applied to obtain a conversion factor for features that are not one-dimensional.

In a specific implementation, the conversion factor takes the form of a table that relates different CD variation values to different intensity variation values. In another technique, the k factor takes the form of an equation that can be applied to an intensity variation value to obtain a CD variation value. Regardless, the measured intensity variation values from the test image can be effectively converted to CD variation values for each FOV measured position. For example, this conversion factor k can be used to determine CD variation for different field of view (FOV) positions of the test image to generate a CDU map in operation 310.

Based on the design data, the CD changes for different FOV positions due to flare compensation may be determined to generate a flare map in operation 312. For instance, the CD differences between similar types of pattern features (e.g., line patterns) may be determined across the reticle. In another approach, CD differences are typically added to the design data in an EDA (electronic design automation) operation, and both the pre- and post-correction (such as post-flare correction) design data may be provided in order to determine the CD compensation values. In a specific embodiment, the pre-correction design data's CD is compared to the post-correction design data's CD, and such CD difference is defined as a correction (e.g., flare) map. This correction CD map may then be subtracted from the CDU map that was determined for the test image in order to then determine the actual CDU map for the EUV reticle under test (without flare compensation) in operation 314.

Pattern orientation may also be factored into the process for determining a CDU map so as to separately consider such pattern differences. For example, a design template may be used to specify particular pitch and orientation values for particular reticle portions. Alternatively, the design data patterns may be analyzed to locate particular patterns, such as one dimensional horizontal or vertical lines or spaces. For example, different conversion factors can be generated for different reticle areas that have different pitch and orientations. In a specific implementation, vertical features are analyzed separately from horizontal features since the orientation of the features with respect to an angled incident beam will affect the reflected intensity differently, referred to as the "shadow effect" on the EUV scanner. As a result, even though certain patterns are intended to be the same on the final wafer regardless of their orientations, those patterns on the EUV reticle will have substantially different sizes depending on their orientation. Therefore, their conversion factor (k) can be different enough that horizontal and vertical features can be considered separately in the construction of CDU map through intensity measurements. That is, the correction CD map for the horizontal features can be obtained separately from the correction CD map for the vertical features. These separate correction maps can then be separately subtracted from the CDU maps obtained from the respective test image features. The final, separated CDU maps can then be combined or kept separate for correction of the photolithography process.

After a CDU map is provided, it may be determined whether the reticle passes inspection based on such map in operation 316. For instance, a user may analyze the amount of CD variation to determine whether such CD variance is within a predefined specification. Alternatively, an automated process may determine whether any CD variation is above (or below) a predefined threshold. If CD variation is above (or below) the predefined threshold, the corresponding reticle portion may then be more carefully reviewed to determine whether the reticle is defective and can no longer be used. For instance, a SEM may be used to review the defective area to determine whether critical dimensions (CD's) are actually out of specification.

If the reticle passes inspection/measurement, such reticle may be used for fabricating a wafer in operation 320. An accurately determined CDU map may also be utilized to effectively manage the dose levels across the reticle during fabrication of a wafer using such reticle. For instance, the CDU map for particular positions on the reticle is mapped to dose corrections in the photolithography light for such particular positions of the reticle.

If the reticle fails inspection/measurement, the reticle may be discarded or repaired if possible in operation 318. For instance, certain defects can be cleaned or removed from the reticle. After repair, an inspection may be performed on the reticle at any time and the procedure 300 repeated. One such repair tool is Zeiss's CDC tool.

This design database approach can enable use of the features that are best suited for intensity-based CD characterization. Additionally, since a "good" design is used to simulate the particular reticle-making process and inspection tool that were used for the reticle under test so that process and tool effects are cancelled out, this approach has low sensitivity to system aberrations or noise (e.g., focus errors). This approach will likely work well with line, spacing, and contact features.

For inspection/metrology systems for which a design data base is not available or processing time and resources are limited, another approach for determining CD uniformity may be utilized. In one approach, a conversion factor (e.g., conversion tables) is pre-computed based on a sample reticle having known CD variation. The design database for this sample reticle may also be available. However, the pre-computation can be performed a single time and then used for other test reticles having patterns that differ from the sample reticle without use of a design database for such test reticle.

Figure 4:
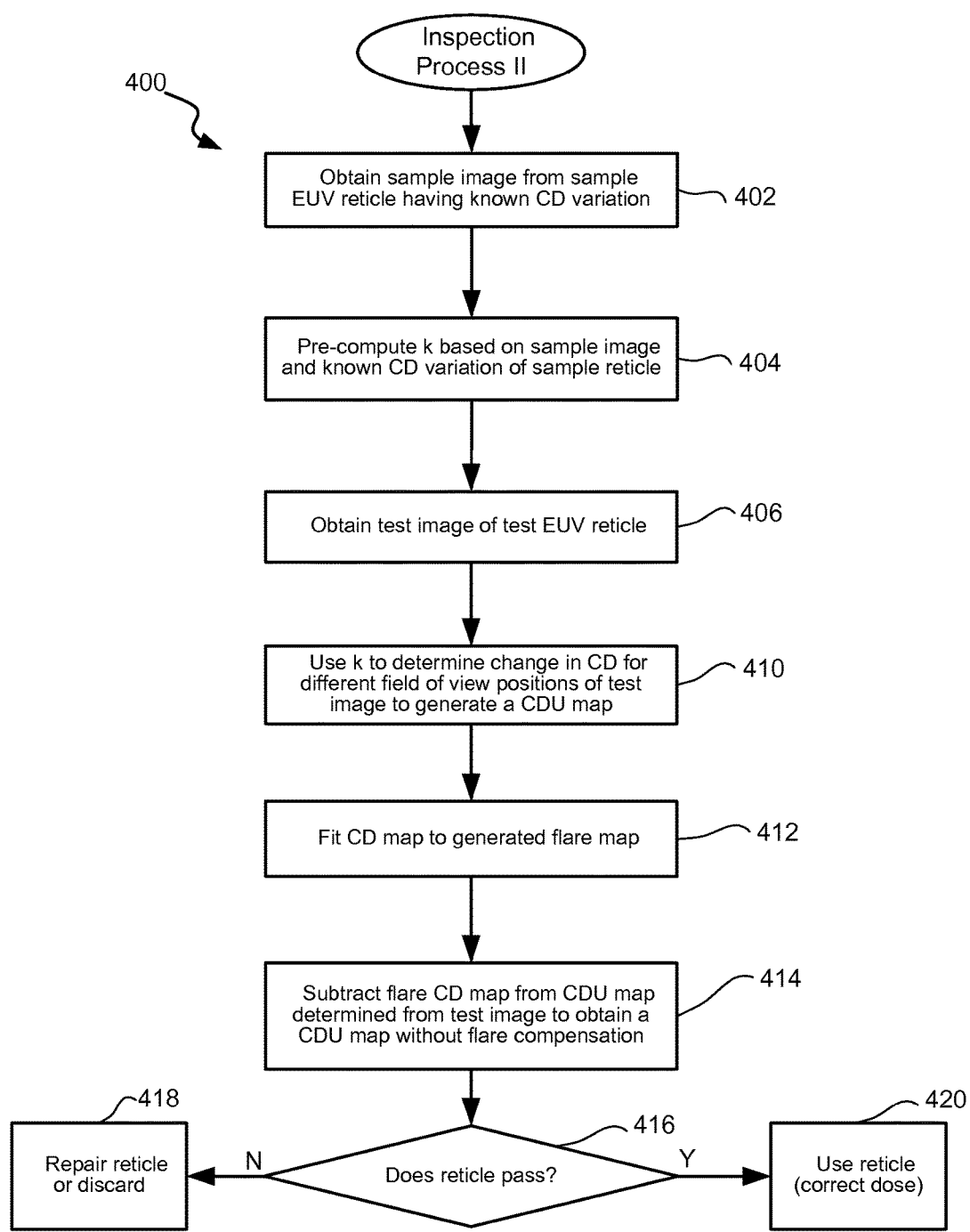
FIG. 4 is a flow chart illustrating a procedure for inspecting an EUV reticle in accordance with a second implementation of the present invention.

FIG. 4 is a flow chart illustrating a procedure for inspecting an EUV reticle in accordance with a second implementation of the present invention. Initially, a sample image is obtained from a sample EUV reticle having known CD variation in operation 402. This sample reticle may have any number and type of patterns having different CD variations, which may or may not include CD variation for flare compensation. This sample image may be used to pre-compute a conversion factor (e.g., in the form of conversion tables) based on the known CD and the measured intensity of sample reticle in operation 404.

The conversion factor may then be stored for later use with other reticle designs. However, a new set of conversion factors are preferably pre-computed for each particular mask-making process, mask materials, and inspection tool so as to achieve an optimum set of conversion factors for the particular processes used for the test reticles. These test reticles can be associated with a tool health calibration process, during which optical images from these test reticles (along with their databases) can be used to determine the conversion factor.

For each new reticle under inspection/measurement, a test image may be obtained, for example, in operation 406. The pre-computed conversion factor k may be used to determine change in CD for different FOV positions of the test image to generate a CDU map in operation 410 as described above.

The CDU map may then be fitted to a generated flare map across the reticle in operation 412. In general, any type of curve fitting technique can be used. Since CD for flare compensation tends to vary across the reticle in a parabola shape (convex or concave), the determined CDU curve can be fitted to a polynomial flare compensation curve that is adjusted based on a least-squares (or minimum squared distance) approach. Other curve fitting approaches may include using a Fourier series or a summation of any number and type of functions as the generated flare curve, implementing algebraic or geometric fitting, etc.

In one example, a difference between the determined CDU map and an adjustable map of CD compensation for flare may be minimized. The quantity that is minimized can be expressed as $\Sigma_{x,y}[\Delta CD(x,y)/CD(x,y)-f(coeff, F(x,y))]^2$, where the summation is taken over the points of the CDU map, and f(coeff, F) is a polynomial of F. F(x,y) is a map of the flare intensity. In one embodiment, F is estimated by first calculating a map of pattern density and then convolving the pattern density map with a point-spread function. The function f(coeff, F(x,y)) is the estimate of the CD compensation for the flare. By minimizing the difference, the set of polynomial coefficients "coeff" can be deduced. In a specific example, F is the flare map and $c*F-d*F^2$ is the relative CD change to compensate for such flare, where c and d are deduced.

Figure 5:
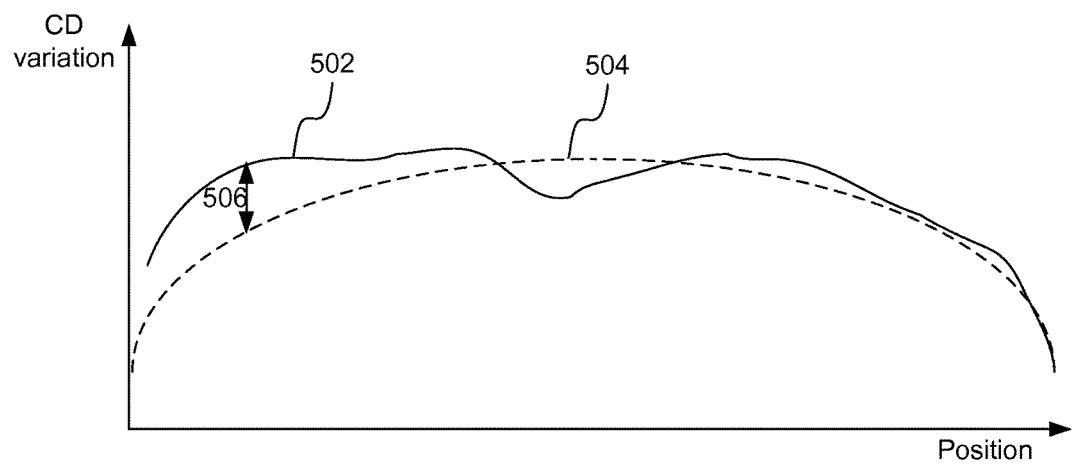
FIG. 5 is a diagrammatic representation of an optimum fit between a CDU curve that was determined for a test reticle and a deduced CD flare curve in accordance with one embodiment of the present invention.

FIG. 5 is a diagrammatic representation of an optimum fit between a CD variation ($\Delta CD/CD$) curve 502 that was determined for a test reticle and a deduced CD flare curve 504 in accordance with one embodiment of the present invention. Each curve is a plot of CD variation (determined or deduced flare compensation) as a function of reticle position. The illustrated curves go from one edge of the reticle to the other edge.

Once a minimized difference between the CD variation data and the deduced flare curve is found, the differences represent CD variation that does not include flare compensation. The CD variation can be used to construct CDU map. As shown, difference 506 represents a CD variation that is not caused by an intended flare compensation CD variation.

Referring back to FIG. 4, this computed flare map can then be subtracted from the determined CDU map to obtain CDU map without flare compensation in operation 414. For instance, a CDU map without flare compensation is determined by the above equation: ($\Delta CD/CD-f(coeff, F)$), where F is the closest flare map.

It may then be determined whether the reticle passes in operation 416. If the reticle passes, the reticle may be used while correcting the dose based on the CDU map in operation 420. Otherwise, the reticle may be repaired or discarded in operation 418.

Figure 7:
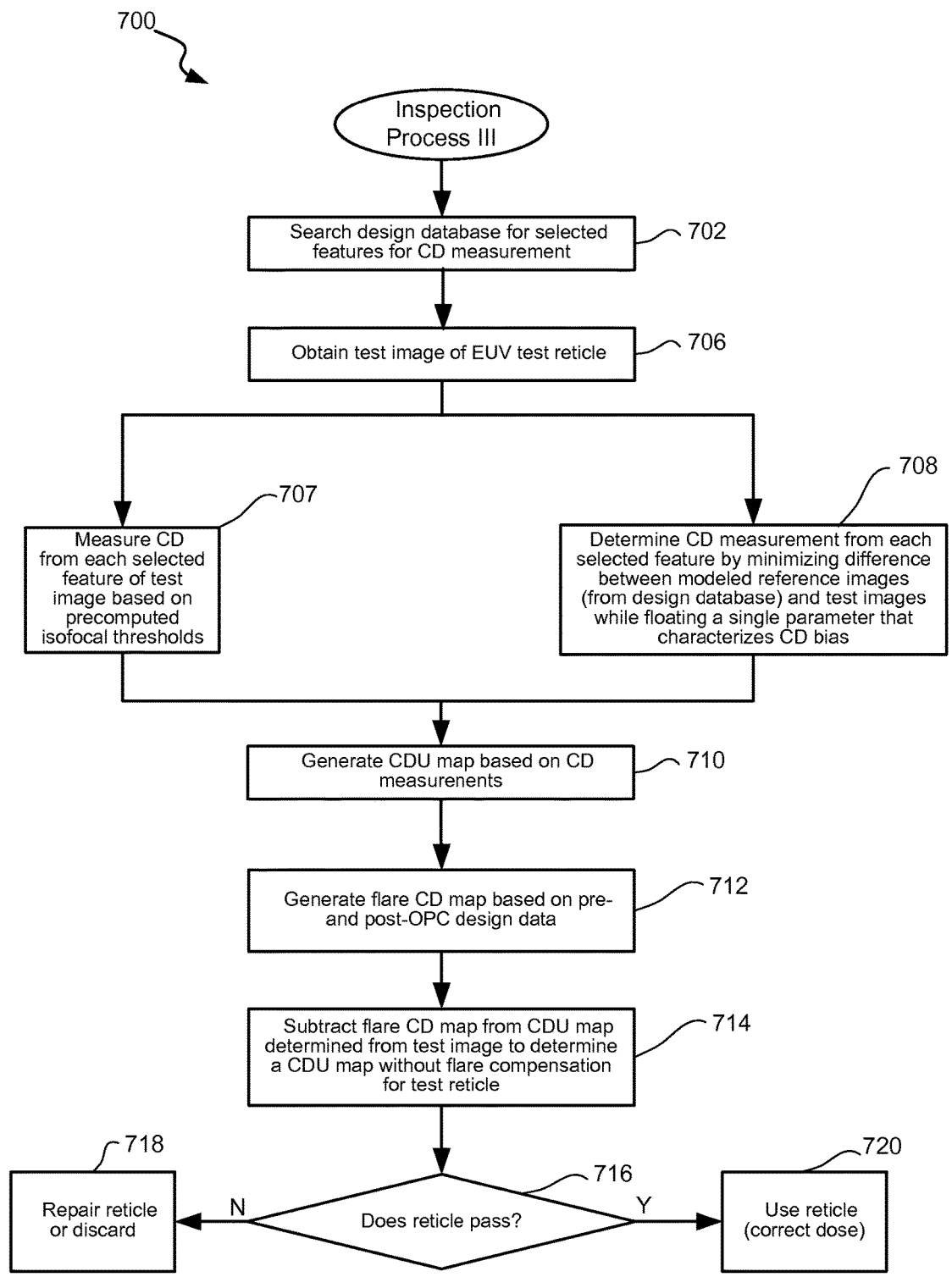
FIG. 7 is a flow chart illustrating a procedure for inspecting an EUV reticle in accordance with a third implementation of the present invention.

In yet another approach, an individual-feature-based CD characterization is used based on a design database. FIG. 7 is a flow chart illustrating a procedure for inspecting an EUV reticle in accordance with a third implementation of the present invention. Initially, the design database is searched to locate selected features for CD measurement in operation 702. For instance, one dimensional line or space features are located using a pattern recognition algorithm or a predefined template that specifies appropriate features.

Figure 6:
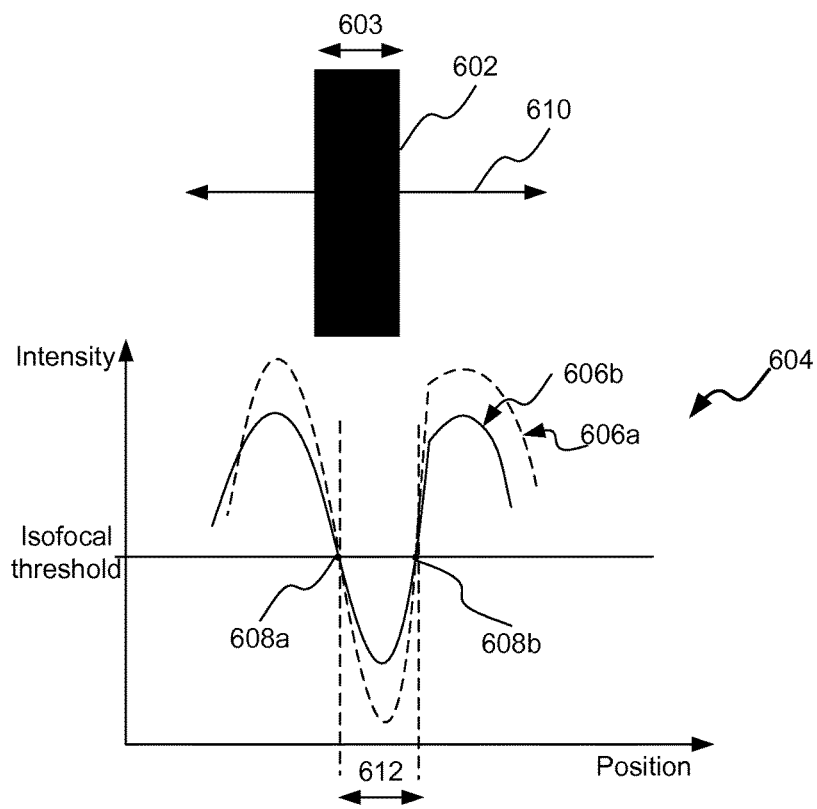
FIG. 6 illustrates obtaining a CD measurement obtained from an intensity image using a pre-computed isofocal threshold.

A test image of the EUV reticle under inspection/measurement may then be obtained in operation 706. Any suitable technique may be used to obtain CD measurements of the selected features of the test reticle. In a first example approach, CD is measured from each selected feature of the test image based on pre-computed isofocal thresholds in operation 707. FIG. 6 illustrates obtaining a CD measurement from an intensity image using a pre-computed isofocal threshold. This FIG. 6 shows using a pre-computed isofocal threshold to measure a CD 603 of a line feature 602 of a test reticle area. Isofocal threshold minimizes sensitivity of CD measurement to focus, and such threshold can be pre-computed from a set of images of the same pattern at different foci.

As shown by intensity curves 606a and 606b for reticle line feature 602, different sets of intensity values may be obtained for the line feature 602 for different focus settings on the inspection tool, for example. Although the intensity values for such line feature 602 may shift up or down with respect to focus setting, there is a isofocal threshold intensity value at which the different intensity curves intersect at two places, which may be used to measure CD. Said in another way, if intensity is measured at a plurality of positions along a line 610 that is perpendicular to the line feature 602 and the isofocal threshold is known, CD can be measured as the position distance 612 between the intensity value points 608a and 608b that are equal to such isofocal threshold. Thus, CD measurements across the reticle may be obtained from intensity values for line features (or other types of features) across the test reticle image.

In a second approach as shown in operation 708 of FIG. 7, a CD measurement for each selected feature may be determined by minimizing the difference between a modeled reference image based on the design data and the test image by adjusting a single model parameter that characterizes CD bias. An adjustable CD bias can be applied to the design data, and the reference image is calculated using the final model, based on the current value of the CD bias. The reference image is the image that is expected to be observed with the inspection tool/microscope when the actual CD bias equals the assumed value of the adjustable CD bias. The value of the CD bias that minimizes a norm of the difference between the reference image and the test image can be defined as the best estimate, e.g., the measurement, of the CD bias. In one embodiment, the norm of the differences between images can be obtained by summing the squares of pixel by pixel differences of the test and reference images. The CD bias that minimizes the norm can be calculated using the Levenberg-Marquardt algorithm or the Gauss-Newton algorithm.

Regardless of how CD measurements are obtained from the test image, a CDU map may then be generated from the CD measurements in operation 710. For instance, $\Delta CD/CD$ is determined for a plurality of selected feature locations across the reticle. A flare CD map may also be generated based on pre- and post-correction (flare correction) design data (or based on other techniques) in operation 712. This correction CD map may then be subtracted from the CDU map that was determined from the test image so as to determine a CDU map without flare compensation for the test reticle in operation 714.

It may then be determined whether the reticle passes in operation 716. If the reticle passes, the reticle may be used while correcting the dose based on the CDU map in operation 720. Otherwise, the reticle may be repaired or discarded in operation 718.

In this last approach, it is not necessary to acquire large areas of repeating patterns. Accordingly, logic (non-repeating) patterns may be used to generate a CDU map. Additionally, this CD measurement approach for determining a CDU map can be very accurate since suitable features that work best for performing CD measurements or characterization are selected from the design database.

Figure 8:
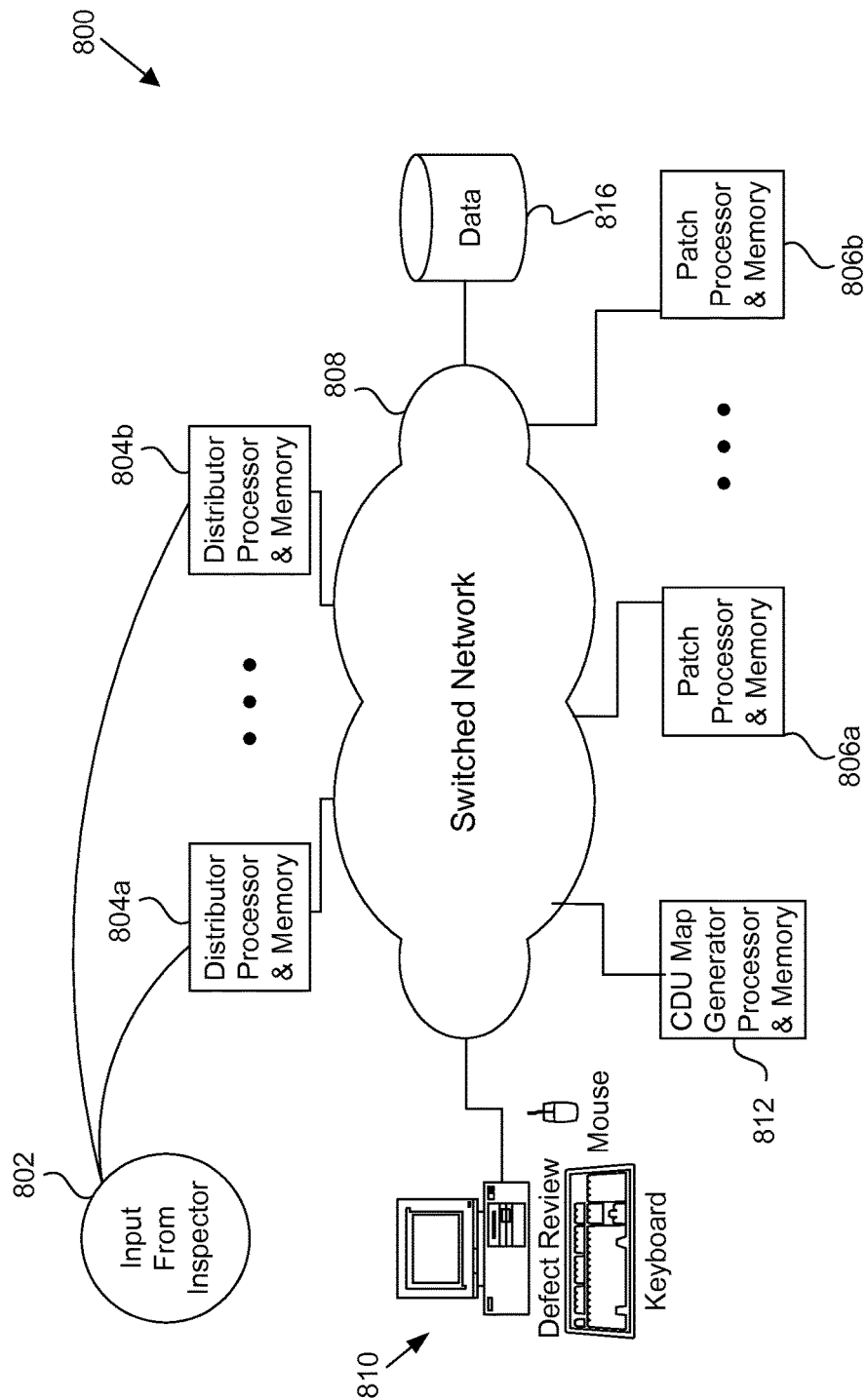
FIG. 8 is a diagrammatic representation of an example inspection system in which techniques of the present invention may be implemented

Techniques of the present invention may be implemented in any suitable combination of hardware and/or software. FIG. 8 is a diagrammatic representation of an example inspection system 800 in which techniques of the present invention may be implemented. The inspection system 800 may receive input 802 from an inspection tool or inspector (not shown). The inspection system may also include a data distribution system (e.g., 804a and 804b) for distributing the received input 802, an intensity signal (or patch) processing system (e.g., patch processors and memory 806a and 806b) for processing specific portions/patches of received input 802, a CDU map generator system (e.g., CDU Map Generator Processor and Memory 812) for generating a CDU map, a network (e.g., switched network 808) for allowing communication between the inspection system components, an optional mass storage device 816, and one or more inspection control and/or review stations (e.g., 810) for reviewing the intensity data, CD measurements, and/or CDU maps. Each processor of the inspection system 800 typically may include one or more microprocessor integrated circuits and may also contain interface and/or memory integrated circuits and may additionally be coupled to one or more shared and/or global memory devices.

The inspection data acquisition system (not shown) for generating input data 802 may take the form of any suitable instrument (e.g., as described further herein) for obtaining intensity signals or images of a reticle. For example, the inspector may construct an optical image or generate intensity values of a portion of the reticle based on a portion of detected light that is reflected off the reticle to one or more light sensors. The inspector may then output the intensity values or image may be output from the inspector.

The inspector or inspection tool may be operable to detect and collect reflected light as an incident optical beam scans across each patch of a reticle. As noted above, the incident optical beam may scan across reticle swaths that each comprises a plurality of patches. Light is collected in response to this incident beam from a plurality of points or subareas of each patch.

The inspection tool may be generally operable to convert such detected light into detected signals corresponding to intensity values. The detected signals may take the form of an electromagnetic waveform having amplitude values that correspond to different intensity values at different locations of the reticle. The detected signals may also take the form of a simple list of intensity values and associated reticle point coordinates. The detected signals may also take the form of an image having different intensity values corresponding to different positions or scan points on the reticle. An intensity image may be generated after all the positions of the reticle are scanned and converted into detected signals, or potions of an intensity image may be generated as each reticle portion is scanned with the final intensity image being complete after the entire reticle is scanned.

In other inspection applications, the incident light or detected light may be passed through any suitable spatial aperture to produce any incident or detected light profile at any suitable incident angles. By way of examples, programmable illumination or detection apertures may be utilized to produce a particular beam profile, such as dipole, quadrapole, quasar, annulus, etc. In a specific example, pixelated illumination techniques may be implemented. Programmable illuminations and special apertures can serve the purpose of enhancing feature contrast for certain patterns on the reticle.

Intensity or image data 802 can be received by data distribution system via network 808. The data distribution system may be associated with one or more memory devices, such as RAM buffers, for holding at least a portion of the received data 802. Preferably, the total memory is large enough to hold an entire swatch of data. For example, one gigabyte of memory works well for a swatch that is 1 million by 1000 pixels or points.

The data distribution system (e.g., 804a and 804b) may also control distribution of portions of the received input data 802 to the processors (e.g. 806a and 806b). For example, data distribution system may route data for a first patch to a first patch processor 806a, and may route data for a second patch to patch processor 806b. Multiple sets of data for multiple patches may also be routed to each patch processor.

The patch processors may receive intensity values or an image that corresponds to at least a portion or patch of the reticle (as well as reference images). The patch processors may each also be coupled to or integrated with one or more memory devices (not shown), such as DRAM devices that provide local memory functions, such as holding the received data portion. Preferably, the memory is large enough to hold data that corresponds to a patch of the reticle. Alternatively, the patch processors may share memory. An example is Intel's multiple CPUs, where each core serves as a patch processor and many cores share the memory.

Each set of input data 802 may correspond to a swath of the reticle. One or more sets of data may be stored in memory of the data distribution system. This memory may be controlled by one or more processors within the data distribution system, and the memory may be divided into a plurality of partitions. For example, the data distribution system may receive data corresponding to a portion of a swath into a first memory partition (not shown), and the data distribution system may receive another data corresponding to another swath into a second memory partition (not shown). Preferably, each of the memory partitions of the data distribution system only holds the portions of the data that are to be routed to a processor associated with such memory partition. For example, the first memory partition of the data distribution system may hold and route first data to patch processor 806a, and the second memory partition may hold and route second data to patch processor 806b.

The data distribution system may define and distribute each set of data of the data based on any suitable parameters of the data. For example, the data may be defined and distributed based on the corresponding position of the patch on the reticle. In one embodiment, each swath is associated with a range of column positions that correspond to horizontal positions of pixels within the swath. For example, columns 0 through 256 of the swath may correspond to a first patch, and the pixels within these columns will comprise the first image or set of intensity values, which is routed to one or more patch processors. Likewise, columns 257 through 512 of the swath may correspond to a second patch, and the pixels in these columns will comprise the second image or set of intensity values, which is routed to different patch processor(s).

The inspection apparatus may be suitable for inspecting semiconductor devices or wafers and optical reticles, as well as EUV reticles or masks. One suitable inspection tool is the Teron™ reticle inspection tool available from KLA-Tencor of Milpitas, Calif. Other types of samples which may be inspected or imaged using the inspection apparatus of the present invention include any surface, such as a flat panel display.

An inspection tool may include at least one light source for generating an incident light beam, illumination optics for directing the incident beam onto a sample, collection optics for directing an output beam that is emitted from the sample in response to the incident beam, a sensor for detecting the output beam and generating an image or signal for the output beam, and a controller for controlling the components of the inspection tool and facilitating the CDU map generation techniques as described further herein.

In the following exemplary inspection systems, the incident beam may be in any suitable form of coherent light. Additionally, any suitable lens arrangement may be used to direct the incident beam towards the sample and direct the output beam emanating from the sample towards a detector. The output beam may be reflected or scattered from the sample or transmitted through the sample. For EUV reticle inspection, the output beam is reflected from the sample. Likewise, any suitable detector type or number of detection elements may be used to receive the output beam and provide an image or a signal based on the characteristics (e.g., intensity) of the received output beam.

Figure 9:
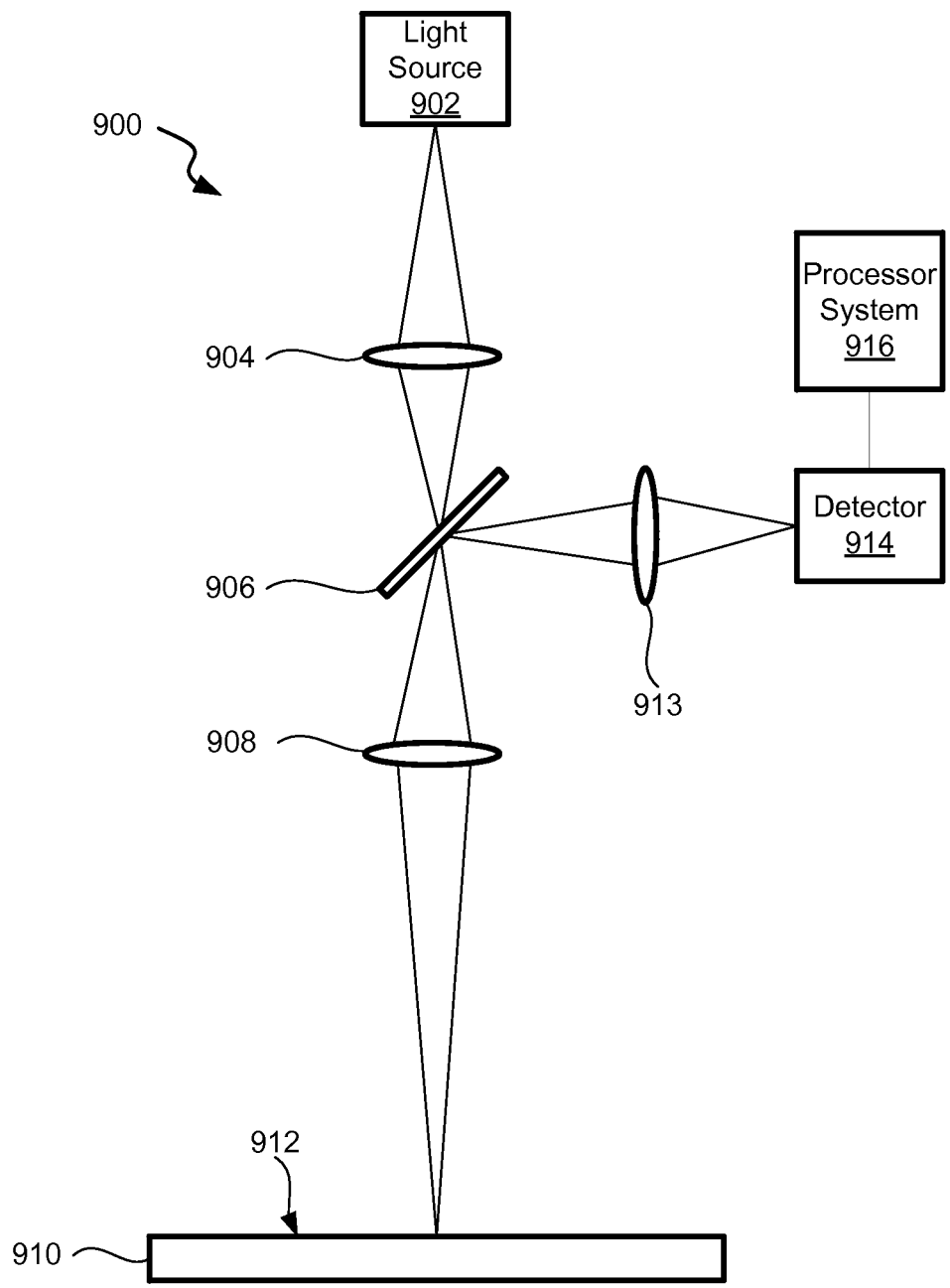
FIG. 9 is a diagrammatic representation of some elements of an optical inspection tool in which techniques of the present invention may be implemented.

FIG. 9 is a diagrammatic representation of some elements of an optical inspection tool in which techniques of the present invention may be implemented. A system 900 includes a light source 902 that is suitable for inspection of an EUV reticle. One example of a light source is a quasi-continuous wave laser. In certain embodiments, a light source may generally provide high pulse repetition rate, low-noise, high power, stability, reliability, and extendibility. It is noted that while an EUV scanner operates at 13.5 nm wavelength, an inspection tool for an EUV reticle does not have to operate at the same wavelength. A Teron™ system from KLA-Tencor operating at 193 nm has been proven to be able to inspect EUV reticles.

A light source may include a beam steering device for precise beam positioning and a beam conditioning device, which can be used to provide light level control, speckle noise reduction, and high beam uniformity. Beam steering and/or beam conditioning devices may be separate physical devices from, for example, a laser.

An inspection system includes a collection of optical elements for focusing an illuminating light beam onto the inspected surface 912. For brevity, FIG. 9 illustrates only a condenser lens 904, an imaging lens 908, a detector lens 913, and a beam splitter 906. However, one skilled in the art would understand that an inspection system can include other optical elements needed to achieve specific inspection functions. The imaging lens 908 may be relatively large in order to meet specific low aberration requirements. The imaging lens can be adjusted to different sizes of pixels, e.g., less than about 100 nm for each pixel or, more particularly, less than about 75 nm or even less than 60 nm.

The sample 910 may also be placed on a stage (not labeled) of the inspection system 100, and the inspection system 100 may also include a positioning mechanism for moving the stage (and sample) relative to the incident beam. By way of examples, one or more motor mechanisms may each be formed from a screw drive and stepper motor, linear drive with feedback position, or band actuator and stepper motor.

After the incident beam(s) impinge on the sample 910, the light may then be reflected and scattered from the sample 910 in the form of "output light" or an "output beam." The inspection system also includes any suitable lens arrangements for directing the output light towards one or more detectors. As shown, a reflected beam can be received by a detector 914. In certain embodiments, the detector is a time delay integration (TDI) detector. A typical TDI detector accumulates multiple exposures of the same area of the inspected surface, effectively increasing the integration time available to collect incident light. The object motion is synchronized with the exposures to ensure a crisp image. In general, a detector may include transducers, collectors, charge-coupled devices (CCDs) or other types of radiation sensors.

FIG. 9 shows an example where an illuminating light beam is directed towards the sample surface 912 at a substantially normal angle with respect to the inspected surface. In other embodiments, an illuminating light beam can be directed at an oblique angle, which allows separation of the illuminating and reflected beams. In these embodiments, an attenuator may be positioned on the reflected beam path in order to attenuate a zero order component of the reflected light beam prior to reaching a detector. Furthermore, an imaging aperture may be positioned on the reflected beam path to shift the phase of the zero order component of the reflected light beam.

A detector is typically coupled with a processor system 916 or, more generally, to a signal processing device, which may include an analog-to-digital converter configured to convert analog signals from the detector 914 to digital signals for processing. The processor system 916 may be configured to analyze intensity, phase, and/or other characteristics of one or more reflected beams. The processor system 916 may be configured (e.g., with programming instructions) to provide a user interface (e.g., a computer screen) for displaying a resultant test image and other inspection characteristics. The processor system 916 may also include one or more input devices (e.g., a keyboard, mouse, joystick) for providing input. The processor system 916 may also be coupled with the stage 910 for controlling, for example, a sample position (e.g., focusing and scanning) and other inspection parameters and configurations of the inspection system elements. In certain embodiments, the processor system 916 is configured to carry out inspection techniques detailed above. The processor system 910 typically has one or more processors coupled to input/output ports, and one or more memories via appropriate buses or other communication mechanisms.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

It should be noted that the above description and drawings are not to be construed as a limitation on the specific components of the system and that the system may be embodied in many other forms. For example, it is contemplated that the inspection or measurement tool may have any suitable features from any number of known imaging or metrology tools arranged for detecting defects and/or resolving the critical aspects of features of a reticle or wafer. By way of example, an inspection or measurement tool may be adapted for bright field imaging microscopy, dark field imaging microscopy, full sky imaging microscopy, phase contrast microscopy, polarization contrast microscopy, and coherence probe microscopy. It is also contemplated that single and multiple image methods may be used in order to capture images of the target. These methods include, for example, single grab, double grab, single grab coherence probe microscopy (CPM) and double grab CPM methods. Non-imaging optical methods, such as scatterometry, may also be contemplated as forming part of the inspection or metrology apparatus.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the defect detection characteristic data may be obtained from a transmitted, reflected, or a combination output beam. Accordingly, the present embodiments are to be considered as illustrative and not restrictive, and the invention is not to be limited to the details given herein.

What is claimed is:

1. A method of inspecting an extreme ultraviolet (EUV) reticle using an inspection tool, the method comprising:
   with an inspection tool, obtaining a test image or signal from an EUV test reticle, wherein the test image or signal specifies an intensity variation across the EUV test reticle;
   converting the intensity variation of the test image or signal to a critical dimension (CD) variation across the EUV test reticle so as to generate a critical dimension uniformity (CDU) map, wherein the CDU map is generated by removing correction CD differences that were added to identically designed patterns in the design data to compensate for differences in exposed CD patterns for such identically designed patterns that would otherwise result from different scattering effects for different positions of a field of view (FOV) of a photolithography tool during a photolithography process for exposing CD patterns; and
   storing the CDU map in one or more memory devices or displaying the CDU map on a display device.

2. The method of claim 1, wherein the different scattering effects include different light portions produced by the photolithograph tool having different scattering properties for the identically designed patterns as a function of FOV position prior to adding the correction CD differences wherein the correction CD differences are added so as to result in identically exposed patterns from such identically designed patterns and their correction CD differences.

3. The method of claim 1, wherein the CDU map is generated so as to account for vertical or horizontal feature bias.

4. The method of claim 1, wherein the test image is obtained with the inspection tool at a deep ultraviolet (DUV) wavelength.

5. The method as recited in claim 1, wherein the CDU map is generated by:
   based on the design data for the EUV test reticle, determining a conversion factor for converting between intensity variation and CD variation;
   converting the intensity variation of the test image into a CD variation for such test image;
   based on the design data, determining the correction CD differences; and
   subtracting the correction CD differences from the CD variation for the test image to generate the CDU map.

6. The method of claim 5, wherein the conversion factor is determined by performing electromagnetic simulations by applying a model on the design data so as to model construction of a reticle from such design data and so as to model inspection of such reticle to generate a reference image that substantially matches the test image.

7. The method of claim 6, wherein the CD variation of the test image specifies a dominant or average CD value for each of a plurality of positions of the EUV reticle with respect to a global average or dominant CD value for such EUV reticle.

8. The method of claim 7, wherein the conversion factor takes the form of a table of associated intensity and CD variation values.

9. The method of claim 1, wherein the correction CD differences are determined by determining a CD difference between pre-correction design data that would result in identical patterns having different exposed patterns for different FOV positions and post-correction design data for minimizing such different exposed patterns.

10. An inspection system for inspecting an EUV reticle, comprising:
    a light source for generating an incident beam;
    an illumination optics module for directing the incident beam onto an EUV reticle;
    a collection optics module for directing an output beam that is reflected from the EUV reticle in response to the incident beam;
    a sensor for detecting the output beam and generating an image or signal for the output beam; and
    a controller that is configured to perform the following operations:
      obtaining a test image or signal from an EUV test reticle in response to the incident beam, wherein the test image or signal specifies an intensity variation across the EUV test reticle;
      converting the intensity variation of the test image or signal to a critical dimension (CD) variation across the EUV test reticle so as to generate a critical dimension uniformity (CM) map, wherein the CDU map is generated by removing correction CD differences that were added to identically designed patterns in the design data to compensate for differences in exposed CD patterns for such identically designed patterns that would otherwise result from different scattering effects for different positions of a field of view (FOV) of a photolithography tool during a photolithography process for exposing CD patterns; and
      storing the CDU map in one or more memory devices or displaying the CDU map on a display device.

11. The system of claim 10, wherein the different scattering effects include different light portions produced by the photolithograph tool having different scattering properties for the identically designed patterns as a function of FOV position prior to adding the correction CD differences wherein the correction CD differences are added so as to result in identically exposed patterns from such identically designed patterns and their correction CD differences.

12. The system of claim 10, wherein the CDU map is generated so as to account for vertical or horizontal feature bias.

13. The system of claim 10, wherein the test image is obtained with the inspection tool at a deep ultraviolet (DUV) wavelength.

14. The system as recited in claim 10, wherein the CDU map is generated by:
- based on the design data for the EUV test reticle, determining a conversion factor for converting between intensity variation and CD variation;
- converting the intensity variation of the test image into a CD variation for such test image;
- based on the design data, determining the correction CD differences; and
- subtracting the correction CD differences from the CD variation for the test image to generate the CDU map.

15. The system of claim 14, wherein the conversion factor is determined by performing electromagnetic simulations by applying a model on the design data so as to model construction of a reticle from such design data and so as to model inspection of such reticle to generate a reference image that substantially matches the test image.

16. The system of claim 15, wherein the CD variation of the test image specifies a dominant or average CD value for each of a plurality of positions of the EUV reticle with respect to a global average or dominant CD value for such EUV reticle.

17. The system of claim 16, wherein the conversion factor takes the form of a table of associated intensity and CD variation values.

18. The system of claim 14, wherein the correction CD differences are determined by determining a CD difference between pre-correction design data that would result in identical patterns having different exposed patterns for different FOV positions and post-correction design data for minimizing such different exposed patterns.

* * * * *